United States Patent [19]

Bulou et al.

[11] Patent Number: 5,457,987
[45] Date of Patent: Oct. 17, 1995

[54] SURFACE TENSION SENSOR

[75] Inventors: Jacques Bulou, Saint Remy; Jean-Marie Raynal, Vitry-sur-Seine, both of France

[73] Assignee: Eastman Kodak Company, Rochester, N.Y.

[21] Appl. No.: 204,229

[22] PCT Filed: Sep. 18, 1992

[86] PCT No.: PCT/EP92/02158

§ 371 Date: Mar. 4, 1994

§ 102(e) Date: Mar. 4, 1994

[87] PCT Pub. No.: WO93/06453

PCT Pub. Date: Apr. 1, 1993

[30] Foreign Application Priority Data

Sep. 23, 1991 [FR] France .................................. 91 11953

[51] Int. Cl.⁶ ........................................................ G01N 13/02
[52] U.S. Cl. ........................................ 73/64.490; 73/54.01
[58] Field of Search ............................. 73/64.49, 64.51, 73/64.48, 64.49, 64.51, 64.48, 54.01

[56] References Cited

U.S. PATENT DOCUMENTS

| | | | |
|---|---|---|---|
| 2,756,587 | 7/1956 | Doble | 73/64.49 |
| 3,415,109 | 12/1968 | Sucker et al. | 73/64.49 |
| 3,504,530 | 4/1970 | McConnell | 73/64.49 |
| 3,780,569 | 12/1973 | Graham | 73/64.4 |
| 4,437,337 | 3/1984 | Fenrick | 73/54 |
| 4,646,562 | 3/1987 | Cronan | 73/64.4 |
| 4,970,893 | 11/1990 | Reid | 73/64.4 |

FOREIGN PATENT DOCUMENTS

| | | | |
|---|---|---|---|
| 549812 | 4/1982 | Australia . | |
| 975590 | 3/1951 | France . | |
| 1254889 | 11/1964 | Germany . | |
| 9231437 | 12/1984 | Japan | 73/64.49 |
| 0545905 | 2/1977 | U.S.S.R. | 73/64.49 |

OTHER PUBLICATIONS

Article re precise measurement of density and surface tension at temps up to 1000° C. Review of Scientific Instruments, vol. 31, No. 1, Jan. 1960, pp. 18–22 Article from the Journal of Physics E. Scientific Instruments.

Primary Examiner—Hezron E. Williams
Assistant Examiner—J. David Wiggins
Attorney, Agent, or Firm—Carl F. Ruoff

[57] ABSTRACT

The invention relates to a surface tension sensor for a liquid flow. The device according to the present invention includes a measuring probe formed of a wettable cylinder, the cross section circumference of which does not exhibit any concave portion and the distance of which between the isobaricenter of the cross section and any point on the circumference is less than 3 mm, the ratio between the maximum distance of a point on the circumference to the isobaricenter and the minimum distance of a point on said circumference to the isobaricenter being less or equal to 2. Application relates to the surface tension measuring of photographic compositions on a photographic coating device.

4 Claims, 3 Drawing Sheets

SURFACE TENSION SENSOR

FIELD OF THE INVENTION

The invention relates to a surface tension measuring device for a liquid, and relates more particularly to the surface tension measuring of a liquid flow on an horizontal or slightly inclined plane. This device according to the invention is particularly adapted for measuring the surface tension of a photographic emulsion on the inclined plane of a coating device, or of a surfactant solution.

BACKGROUND OF THE INVENTION

According to a known technique, known as WILHELMY technique, the surface tension of a static liquid is measured by means of a very thin and rectangular platinum blade passing through the surface to be studied. The platinum blade is suspended at one end of a wire and brought into contact of the liquid surface. FIG. 1 to which is now referred to, schematically illustrates a device carrying out the WILHELMY technique. The device comprises a platinum blade 1, the dimensions of which, by way of example, can be of 2 cm wide, 1 cm high and 0.01 cm thick. This blade is coupled to a balance 2 or a strain gauge by means of a wire 3.

Let us sum up briefly the theory which governs the operation of such a surface tension sensor. When a perfectly wettable platinum blade 1 is dipped into a liquid 4, this blade is subjected to capillary forces S and to buoyancy $P_A$. The buoyancy corresponds to the volume immerged multiplied by the density. In the case of a conventional surface tension measuring of a static liquid, the immersion height of the blade is null; the $P_A$ force is thus null. In order to extract this blade out of the liquid, a vertical outwardly oriented force f must be exerted, proportional to the blade perimeter and to the liquid surface tension $\sigma$. This last parameter depends on the liquid, and is constant for a pure liquid, for a given temperature. For surfactant solutions, this parameter depends on the concentration and the age of the surface.

The equation governing the equilibrium of the forces is the following:

$$F = S - P_A \quad (1)$$

$$\text{with } S = \sigma . L . \cos\theta = m.g \quad (2)$$

wherein:

$\theta$ is the liquid/solid wetting angle. For a perfectly wettable sensor, the solid/liquid wetting angle is equal to zero. So, we have $\cos\theta = 1$.

m is the compensation mass of the desequilibrium in grams g is the acceleration of gravity: $9.81 \cdot 10^{-3}$ N.s$^{-2}$.

$\sigma$ is the surface tension in dyn.cm$^{-1}$.

L is the length in cm whereon the meniscus is caught, i.e., the perimeter of the blade portion in contact with the liquid.

Thus, we have:

$$\sigma = \frac{m \cdot g}{L \cdot \cos\theta} = \frac{m \cdot g}{L}$$

This technique is perfectly satisfactory when it deals with the surface tension measuring of a static liquid but raises problems for the surface tension measuring of a flow on a horizontal or slightly inclined plane, the measures being in fact erroneous due to the drag force acting on the blade. This was demonstrated in an Article of R. DEFAY and J. HOMMELEN published in the journal de l'industrie Belge (23, Jun. 1958, pages 597–614). On page 602, paragraph 6, it is mentioned that the ascending and drag forces have always been too important to be able to provide for an even approximative measure of the surface tension.

According to another known method which raises the same problems, the rectangular blade was replaced by a ring.

Thus, it is an object of the present invention to provide a device allowing an experimenter to measure the surface tension of a liquid, particularly adapted to a flow on a horizontal or slightly inclined plane.

SUMMARY OF THE INVENTION

Other objects of the present invention will appear during the detailed following disclosure. The objects of the present invention will be achieved by means of a surface tension sensor for a liquid flow including a means allowing an experimenter to measure a force, and a probe which is brought into contact with the liquid, said probe being hooked to the means measuring the force by means of an appropriate member, said device being characterized in that the probe, at least in its portion being into contact with the liquid, is comprised of a wettable cylinder, the cross section circumference of which does not exhibit any concave portion and whose distance between the cross section isobaricenter and any point on the circumference is less than 3 mm, the ratio between the maximum distance of a point on the circumference to the isobaricenter and the minimum distance of a point on the circumference to the isobaricenter being less or equal to 2.

According to an embodiment, the probe is comprised of a solid figure of revolution cylinder. Advantageously, the cylinder diameter is less or equal to 5 mm, and preferably, of the order of 1 mm. According to another alternative of the present invention, the probe is comprised of a platinum wire.

BRIEF DESCRIPTION OF THE DRAWINGS

During the detailed following disclosure, reference will be made to the drawings, wherein.

DETAILED DESCRIPTION OF THE PREFERRED EMBODIMENTS

Figure 1:
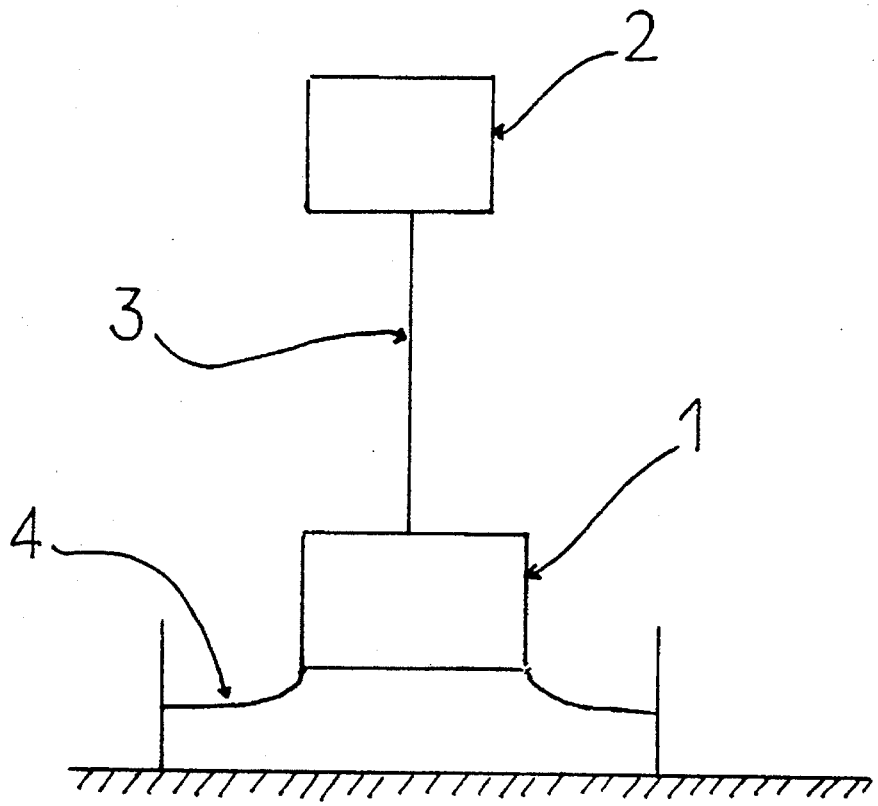
FIG. 1 illustrates a surface tension sensor, such as disclosed in the prior art.
Figure 2:
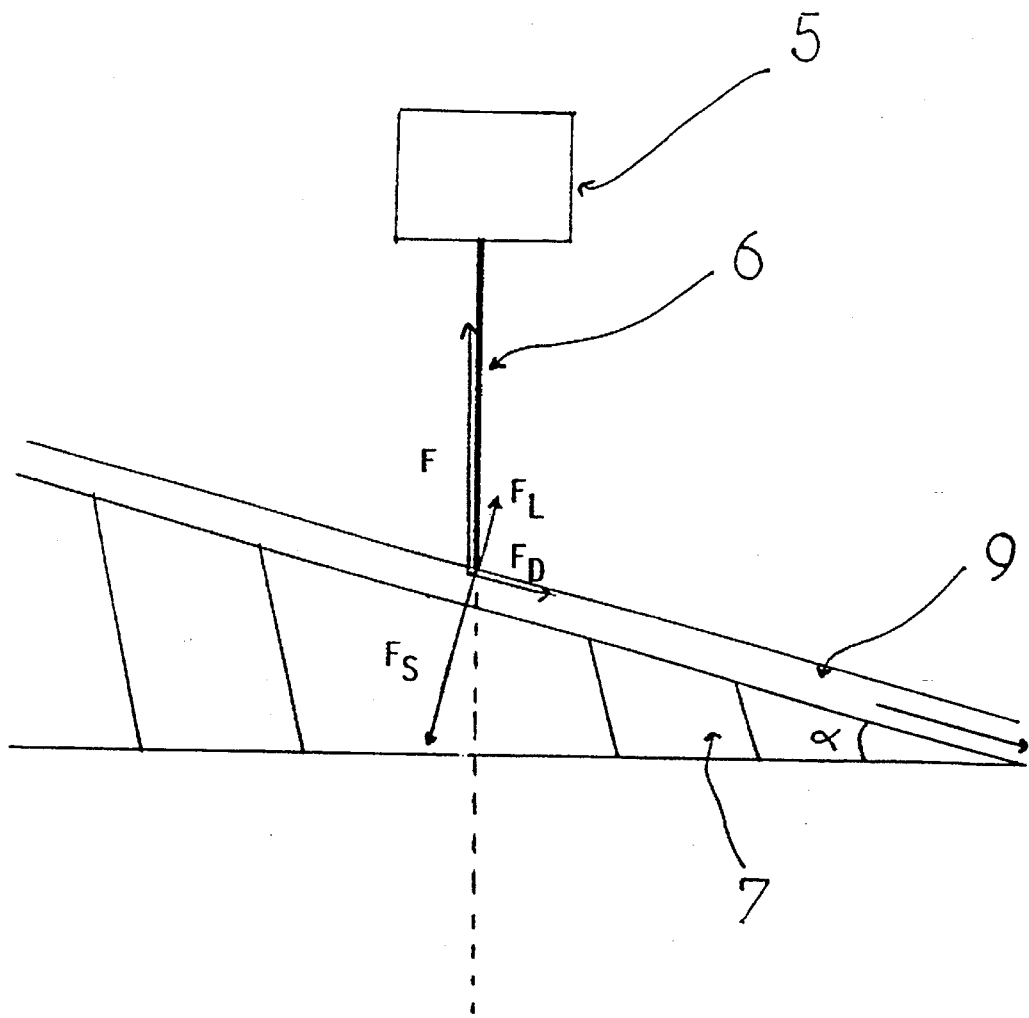
FIG. 2 illustrates a surface tension sensor according to the present invention.

According to the present invention, the surface tension measuring device, illustrated in FIG. 2, is mainly comprised of a means 5 capable to measure a force, the amplitude of which is relatively low and can vary, by way of example, from $5 \cdot 10^{-5}$ to $30 \cdot 10^{-5}$ N. According to an embodiment, this measuring device is comprised of an electronic balance of the type Cahn® 2000 or a conventional force meter of the Schenck® type. These devices are well known in the art and do not require a more detailed disclosure.

The device also includes a measuring probe 6 hooked to the force meter 5 and which is brought into contact with a liquid 9 flowing on a plane 7, which, according to the embodiment illustrated, is slightly inclined; preferably, the inclination is less than 45°. Good results were obtained for an inclination angle less than 20°. It is obvious that such a device also finds application for measuring the surface tension of a liquid moving on a horizontal plane. Such is the case when the surface tension of a photographic emulsion, when coated on a moving web, is measured. The measuring probe 6 according to the present invention is comprised of a wettable cylinder which, at least in its portion brought into contact with the liquid, is such that the circumference of its cross section does not exhibit any concave portion and that the distance between the isobaricenter of the cross section and any point on the circumference is less than 3 mm, the ratio between the maximum distance of a point on the circumference to the isobaricenter and the minimum distance of a point on said circumference to the isobaricenter being less or equal to 2. Advantageously, the probe is comprised of a solid figure of revolution cylinder, the diameter of which is less or equal to 5 mm, and preferably, of the order of 1 mm. In reality, it is preferable that the cylinder exhibits a symmetry axis with respect to the liquid flow. In fact, this facilitates the measurement (reduces the noise) and reduces at the minimum the drag forces. This point will be developed more in detail therafter.

Now, let us study such a device with respect to the measured forces. Force F, sensed by the force meter, in the case of a plane inclined of an angle α with respect to the horizontal, includes three main components: a force corresponding to the component, according to the probe axis, of force $F_s$ due to the surface tension; a force illustrating the component according to the probe axis of drag force $F_D$ due to the liquid flow; a force corresponding to the component, according to the probe axis, of force $F_L$ due to the buoyancy.

At equilibrium, we have:

$$F = F_s \cos \alpha + F_D \sin \alpha - F_L \cos \alpha$$

Force $F_L$, directly connected to the buoyancy (ascending force), is perpendicular to the flow velocity and is proportional to the volume immerged as well as the flow velocity.

In our measures, we consider that the volume immerged is negligible and thus that $F_L$ is also negligible.

As regards to the drag force, this one depends on the probe cross section, but also on the viscosity of the liquid and on the surface velocity of the liquid.

In the case of a cylindrical solid exhibiting a radius r, brought into contact with a fluid having a surface velocity V, the value of force $F_D$ relative to the resistance to the flow of a solid (due to the pressure difference between the leading edge and the trailing edge of the solid) in an incompressible fluid medium, is given by relation:

$$F_D = C \cdot S \cdot \frac{p \cdot V^2}{2}$$

wherein:
p is the volumetric mass;
S is the main frame surface, i.e., the projection surface of the solid on a plane perpendicular to the velocity;
V is the surface velocity of the liquid;
C is the shape factor and depends on the fluid viscosity, the solid shape and the fluid velocity. This value of C depends on the Reynolds number for simple geometrical shapes. In the case of a revolution cylinder, having a diameter 2r in a liquid, the velocity of which is normal to its generatrices, the value of C=1,2 when the Reynolds number R varies from 50 to 200 000; the Reynolds number being equal to the flow rate/viscosity ratio;
v is the fluid viscosity;

In the case where r=0.1 cm; V=20 cm.s$^{-1}$; p=1; v=10$^{-1}$ P, we have R=200; C=1.2 and $F_D$=7.5.10$^{-5}$N.

In the case where the flow plane of the fluid is inclined of 15°, the component according to the probe axis of the drag force is of 7.5. sin 15°; i.e., 0.25.10$^{-5}$N.

Since the force measured by the sensor varies from 5.10$^{-5}$N and 30.10$^{-5}$N, it can be considered that the drag force is negligible. Force F measured by the sensor can thus be considered as being only the resultant of the surface tension force, i.e:

$$F = F_s \cdot \cos \alpha = \sigma \cdot \frac{2 \pi r}{\cos \alpha} \cdot \cos \alpha = \sigma \cdot 2 \pi r$$

wherein σ is the surface tension to be measured, factor cos α of the denominator being bound to the fact that, on a plane inclined of an angle α, the wet perimeter of a revolution cylinder forms an ellipse and not a circle.

$$\text{i.e. } \sigma = \frac{F}{2 r}$$

Advantageously, the surface tension force is measured when the probe contacts the liquid.

According to an embodiment, the probe according to the present invention is comprised of a platinum wire, the diameter of which is 1 mm.

The lateral surface of the probe end in contact with the liquid must be finely ground, for example by mild sand blasting, in order to obtain a low order of a roughness allowing a perfect wetting of the probe.

Figure 3A:
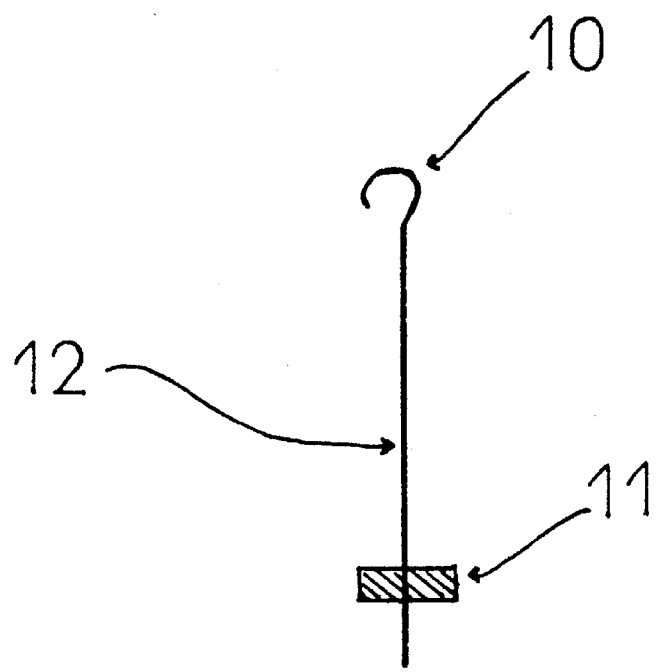
FIGS. 3A–3B illustrate two embodiments of a measuring probe, such as used in the present invention.
Figure 3B:
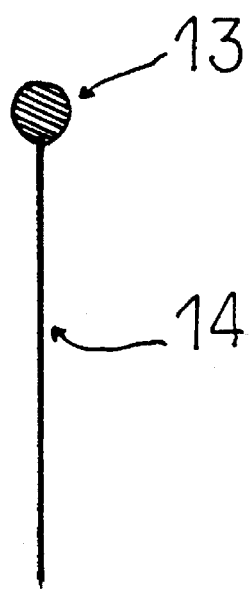

FIG. 3A illustrates an embodiment of the probe according to the present invention. This one includes, at one of its ends, a hook 10 allowing to hang up probe 12 to a precision balance. Likewise, it is preferable to place on the probe a weight 11 at about 1 cm from the end of the probe in contact with the liquid. This weight 11 allows to stabilize more rapidly the probe in a perturbated medium. The end of the probe in contact with the liquid is ground over a length of about 1 cm.

In the embodiment of FIG. 2, one of the ends of probe 14 includes a hooking sphere 13 of the probe to a force meter.

Likewise, for stability reasons, it is preferable that the flow velocity of the fluid is less than 30 meters/minute.

Other materials can also be perfectly appropriate to manufacture the probe according to the present invention. By way of example, stainless steel or plastic can be cited; these materials can become perfectly wettable, for example, by grounding them by sand blasting, at least for the end of the probe in contact with the liquid.

Even if in the preferred embodiment mentionned in the disclosure, the probe is comprised of a revolution cylinder, it is obvious that other shapes can be provided for. By way of example, the probe can be triangular, hexagonal or square.

The device according to the invention is particularly adapted to the surface tension measuring of aqueous flowing surfactant solutions for which the surface tension, contrary to the pure organic liquids, depends on the age of the surface and on the surfactant diffusion velocity towards the free surface (at a given temperature). In particular, such a device is perfectly adapted for studies relative to the dynamic properties of the surfactants, and, in extension, for any coating device such as photographic coating devices.

We claim:

1. Method for measuring the dynamic surface tension of a liquid flow, as formed from liquid having a predetermined age, with a probe having a wettable solid body cylinder, which said cylinder is suspended by support means such that its bottom most part barely establishes solid-to-liquid contact with the top surface of said liquid flow moving around said cylinder to form an ellipically-shaped wet perimeter on said cylinder, where said probe measures a force exercised by the liquid on the wettable cylinder just at the point when the cylinder and the liquid break contact as the cylinder is gradually raised up away from said liquid flow, characterized in that the liquid is flowed on an inclined plane relative to the horizontal, and the probe with wettable cylinder is maintained in a stationery vertical orientation relative to the inclined liquid flow passing by said wettable cylinder.

2. Method according to claim 1, wherein said liquid is flowed on an inclined plane, the inclination of which is less than 45.

3. Method according to claim 1, wherein said liquid is flowed on an inclined plane, the inclination of which is less than 20.

4. Method according to claim 1, wherein the cross section of the wettable cylinder is not circular and the distance between any point of the circumference of said cross section to the gravitational center of said cross section is less than 3 mm and the ratio between the maximum distance of a point on the circumference of said cross section to the gravitational center and the minimum distance of a point on said circumference to said gravitational center is less or equal to 2.

* * * * *

UNITED STATES PATENT AND TRADEMARK OFFICE
CERTIFICATE OF CORRECTION

PATENT NO. : 5,457,987
DATED : 17 October 1995
INVENTOR(S) : Jacques Bulou et al It is certified that error appears in the above-indentified patent and that said Letters Patent is hereby corrected as shown below:

Column 6, line 3, after "45" please insert --°--.
Column 6, line 6, after "20" please insert --°--.

Signed and Sealed this

Twenty-third Day of January, 1996

Attest:

BRUCE LEHMAN

Attesting Officer     Commissioner of Patents and Trademarks